(12) United States Patent
Abe

(10) Patent No.: US 12,011,317 B2
(45) Date of Patent: Jun. 18, 2024

(54) ULTRASONIC DIAGNOSTIC APPARATUS, MEDICAL IMAGE PROCESSING APPARATUS, AND MEDICAL IMAGE PROCESSING METHOD

(71) Applicant: CANON MEDICAL SYSTEMS CORPORATION, Otawara (JP)

(72) Inventor: Yasuhiko Abe, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 70 days.

(21) Appl. No.: 17/151,727

(22) Filed: Jan. 19, 2021

(65) Prior Publication Data
US 2021/0219940 A1    Jul. 22, 2021

(30) Foreign Application Priority Data

Jan. 22, 2020  (JP) ................................ 2020-008628

(51) Int. Cl.
*A61B 8/06*    (2006.01)
*A61B 8/00*    (2006.01)
(Continued)

(52) U.S. Cl.
CPC ............ *A61B 8/065* (2013.01); *A61B 8/0883* (2013.01); *A61B 8/463* (2013.01); *A61B 8/466* (2013.01);
(Continued)

(58) Field of Classification Search
None
See application file for complete search history.

(56) References Cited

U.S. PATENT DOCUMENTS

2009/0216124 A1*  8/2009  Chono ................ G01S 7/52087
                                                    600/443
2012/0116219 A1   5/2012  Miller et al.
(Continued)

FOREIGN PATENT DOCUMENTS

CN       101370431 A     2/2009
JP       2006-109959 A   4/2006
(Continued)

OTHER PUBLICATIONS

Wu et al., "Three-Dimensional Echocardiography: Current Status and Real-Life Applications," (Mar. 2017) Acta Cardiol Sin. Mar. 2017; 33(2): 107-118. (Year: 2017).*
(Continued)

*Primary Examiner* — Joel Lamprecht
*Assistant Examiner* — Ashish S Jasani
(74) *Attorney, Agent, or Firm* — Oblon, McClelland, Maier & Neustadt, L.L.P.

(57) ABSTRACT

An ultrasonic diagnostic apparatus according to an embodiment includes processing circuitry. The processing circuitry is configured to acquire a function index value of each heart chamber for two heart chambers, including the left ventricle, included in a moving image of a heart. The processing circuitry is further configured to generate an image by superimposing a range suggestion image on a two-dimensional coordinate space. In the two-dimensional coordinate space, the processing circuitry allocates the function index value of the each heart chamber to each display dimension corresponding to the each heart chamber and defines the functional index value of the left ventricle as an output coordinate. In the range suggestion image, the processing circuitry colors the range suggestion image according to predetermined normal range and abnormal range for the functional index value of the left ventricle.

14 Claims, 10 Drawing Sheets

(51) Int. Cl.
*A61B 8/08* (2006.01)
*G06T 19/20* (2011.01)

(52) U.S. Cl.
CPC .......... *A61B 8/488* (2013.01); *A61B 8/5207* (2013.01); *G06T 19/20* (2013.01); *G06T 2219/2016* (2013.01)

(56) References Cited

U.S. PATENT DOCUMENTS

| | | | | |
|---|---|---|---|---|
| 2013/0012835 | A1* | 1/2013 | Chono | A61B 8/467 600/587 |
| 2014/0357996 | A1 | 12/2014 | Miller et al. | |
| 2015/0018684 | A1* | 1/2015 | Abe | A61B 8/0883 600/443 |
| 2015/0038846 | A1 | 2/2015 | Abe et al. | |
| 2016/0331349 | A1 | 11/2016 | Abe | |
| 2018/0021024 | A1 | 1/2018 | Fukuda et al. | |
| 2018/0028155 | A1 | 2/2018 | Abe | |
| 2020/0178940 | A1* | 6/2020 | Hare, II | G16H 30/20 |

FOREIGN PATENT DOCUMENTS

| | | |
|---|---|---|
| JP | 2006-153867 A | 6/2006 |
| JP | 2013-517 A | 1/2013 |
| JP | 2013-150730 A | 8/2013 |
| JP | 2015-198672 A | 11/2015 |
| JP | 2016-214393 A | 12/2016 |
| JP | 2018-15150 A | 2/2018 |
| WO | WO-9949775 A2 * | 10/1999 ............... A61B 8/06 |

OTHER PUBLICATIONS

Von Chossy, Claudia, "Tomtec-Arena TM TTA2 Lot 31 Measurement Description," (Aug. 7, 2018), retrieved from <https://www.tomtec.de/fileadmin/user_upload/members-area/downloads/documentation/D.39.0155-08_MeasurementDescription_TTA2.31.pdf> on Jul. 5, 2022. (Year: 2018).*

Kaplan et al., "Distorted assessment of left atrial size by echocardiography in patients with increased aortic root diameter," (Jun. 26, 2021), The Egyptian Heart Journal vol. 73, Article No. 55 (2021). (Year: 2021).*

Linden et al., "Left Atrial Volumes and Phasic Function in Healthy Children: Reference Values Using Real-Time Three-Dimensional Echocardiography," (May 27, 2019), J Am Soc Echocardiogr, Aug. 2019;32(8):1036-1045.e9. (Year: 2019).*

Thebault, C. et al., "Real-time three-dimensional speckle tracking echocardiography: a novel technique to quantify global left ventricular mechanical dyssynchrony," European Journal of Echocardiography, vol. 1, Jan. 12, 2011, doi:10.1093/ejechocard/jeg095, 8 pages.

Combined Chinese Office Action and Search Report dated Jul. 5, 2023 in Patent Application No. 202110072468.1 (with English translation of Category of Cited Documents), 10 pages.

* cited by examiner

ULTRASONIC DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application claims the benefit of priority of Japanese Patent Application No. 2020-008628, filed Jan. 22, 2020, the entire contents of which are incorporated herein by reference.

FIELD

Embodiments described herein relate generally to an ultrasonic diagnostic apparatus, a medical image processing apparatus, and a medical image processing method.

BACKGROUND

In echocardiography using the ultrasonic diagnostic apparatus, cardiac moving images such as two-dimensional (2D) moving images based on 2D scanning and three-dimensional (3D) moving images based on 3D scanning are analyzed by cardiac function analysis technology and myocardial wall motion tracking technology to obtain the function index values, and the cardiac function evaluation is performed using the function index values. As the 2D moving image, for example, a moving image obtained by drawing an apical long axis view such as an A4C image (apical 4-chamber view) or an A2C image (apical 2-chamber view) by 2D scanning may be used. Further, in recent years, it has become possible to obtain various function index values intrinsic to each heart chamber.

However, the displayed image becomes complicated when the function index values of a plurality of heart chambers are displayed on the screen at the same time, and it becomes difficult for the user to grasp the desired function index value and the state of the cardiac function. For example, when displaying information on volume change rate (EF) and longitudinal global strain (GLS) and information on the cavity size for both the left ventricle and the left atrium at the same time, a large number of numerical values are listed on the screen, and thus, it becomes difficult for the user to grasp the displayed image.

In addition, since there are multiple definitions of EF and GLS in the atrium depending on the cardiac time phase, the output information is larger than that of the EF and GLS in the ventricle. Hence, when displaying the EF or GLS of a plurality of definitions of the atrium, the display becomes more complicated and it becomes difficult for the user to evaluate and understand the cardiac function based on the function index value.

DETAILED DESCRIPTION

Hereinbelow, a description will be given of an ultrasonic diagnostic apparatus, a medical image processing apparatus, and a medical image processing method according to embodiments of the present invention with reference to the drawings.

An ultrasonic diagnostic apparatus according to an embodiment includes processing circuitry. The processing circuitry is configured to acquire a function index value of each heart chamber for two heart chambers, including the left ventricle, included in a moving image of a heart. The processing circuitry is further configured to generate an image by superimposing a range suggestion image on a two-dimensional coordinate space. In the two-dimensional coordinate space, the processing circuitry allocates the function index value of the each heart chamber to each display dimension corresponding to the each heart chamber and defines the functional index value of the left ventricle as an output coordinate. In the range suggestion image, the processing circuitry colors the range suggestion image according to predetermined normal range and abnormal range for the functional index value of the left ventricle.

(Overall Configuration)

Figure 1:
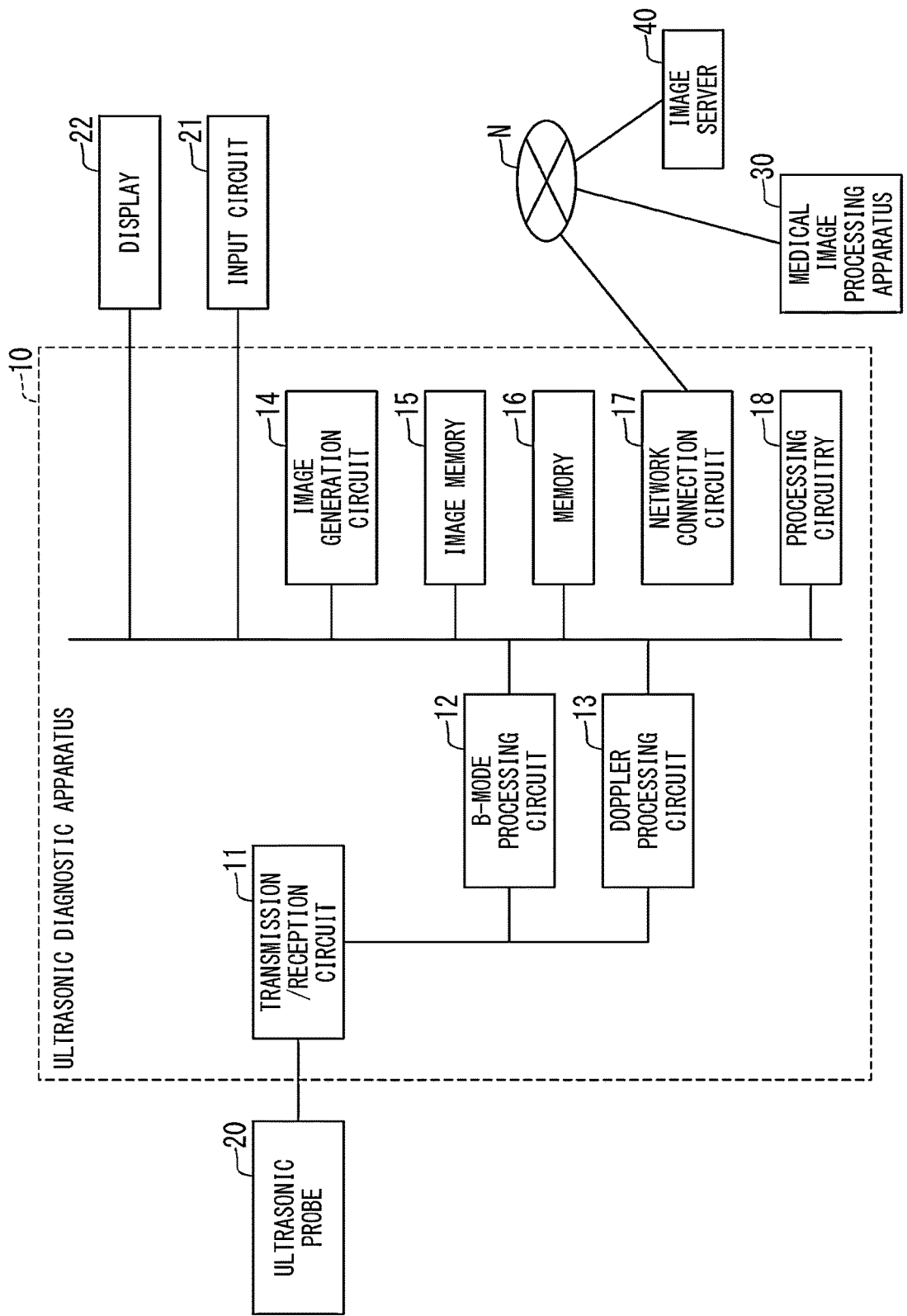
FIG. 1 is a block diagram showing a configuration example of an ultrasonic diagnostic apparatus according to an embodiment.

FIG. 1 is a block diagram showing a configuration example of an ultrasonic diagnostic apparatus 10 according to an embodiment. The ultrasonic diagnostic apparatus 10 may be used by being connected to the ultrasonic probe 20, the input circuit 21, and the display 22. The ultrasonic diagnostic apparatus 10 may include at least one of the ultrasonic probe 20, the input circuit 21, and the display 22. The ultrasonic diagnostic apparatus 10 may be a tablet type or a smartphone type.

The ultrasonic diagnostic apparatus 10 has the transmission/reception circuit 11, the B-mode processing circuit 12, the Doppler processing circuit 13, the image generation circuit 14, the image memory 15, the memory 16, the network connection circuit 17, and the processing circuitry 18.

The transmission/reception circuit 11 has a transmission circuit and a reception circuit. The transmission/reception circuit 11 is controlled by the processing circuitry 18 to control the transmission directivity and the reception directivity in the transmission and reception of ultrasonic waves. Although FIG. 1 shows an example in which the transmission/reception circuit 11 is provided in the ultrasonic diagnostic apparatus 10, the transmission/reception circuit 11 may be provided in the ultrasonic probe 20 or in both the ultrasonic diagnostic apparatus 10 and the ultrasonic probe 20.

The transmitting circuit includes a pulse generator, a transmission delay circuit, and a pulsar circuit, and supplies the ultrasonic transducers with a driving signal. The pulse generator repeatedly generates a rate pulse for forming an ultrasonic wave to be transmitted at a predetermined rate frequency. The transmission delay circuit focuses the ultrasonic wave generated from the ultrasonic transducers into a beam and provides, to each rate pulse generated by the pulse generator, a delay time per ultrasonic transducer that is necessary to determine the transmission directionality.

Additionally, the pulsar circuit applies a driving pulse to the ultrasonic transducers at a timing based on each rate pulse. The transmission delay circuit changes the delay time provided to each rate pulse so as to appropriately adjust a transmission direction of the ultrasonic beam transmitted from the surface of the ultrasonic transducers.

The receiving circuit includes an amplifier circuit, an A/D converter, and an adder circuit. The receiving circuit receives echo signals received by the ultrasonic transducers and generates the echo data by performing various types of processing on the echo signals. The amplifier circuit performs gain correction processing by amplifying the echo signals for each channel. The A/D converter performs A/D conversion on the echo signals subjected to the gain correction processing, and provides the digitized data with a delay time necessary for determining reception directivity. The adder circuit performs addition processing of the echo signals digitized by the A/D converter so as to generate the echo data. Each reflected component from a direction according to reception directivity of each echo signal is enhanced by the addition processing of the adder circuit.

The B-mode processing circuit 12 receives echo data from the receiving circuit and performs logarithmic amplification, envelope detection on the echo data, and the like, so as to generate (B-mode) data expressing the signal intensity by luminance.

The Doppler processing circuit 13 performs frequency analysis on velocity information from the echo data received from the receiving circuit, and extracts a blood-flow component, a tissue component, and a contrast-agent echo component by the Doppler effect. In this manner, the Doppler processing circuit 13 generates data (Doppler data) in which moving-object information items such as the average velocity, variance, and power are extracted for multiple points.

The image generation circuit 14 generates ultrasonic image data on the basis of the echo signals received by the ultrasonic probe 20. For example, the image generation circuit 14 generates two-dimensional B-mode image data in which intensity of each reflected wave is indicated by luminance on the basis of two-dimensional B-mode data generated by the B-mode processing circuit 12. Additionally, the image generation circuit 14 generates image data of a two-dimensional color Doppler image as an average velocity image, a variance image, a power image, a combination image of these images, or the image indicative of the moving-object information, on the basis of the two-dimensional Doppler data generated by the Doppler processing circuit 13.

The image memory 15 is a memory configured to store data of images generated by the processing circuitry 18. The memory 16 is equipped with a configuration including a storage medium that can be read by a processor, such as a magnetic memory medium, an optical memory medium, and a semiconductor memory. The memory 16 may be configured such that some or all of the program and data in those storage media can be downloaded by means of communication via an electronic network N, or can be given via a portable storage medium such as an optical disk. A part or all of the information stored in the memory 16 may be distributed and stored or duplicated in at least one of a storage medium such as an external memory or another memory (not shown) included in the ultrasonic probe 20.

The network connection circuit 17 implements various information communication protocols according to the network N. The network connection circuit 17 connects the ultrasonic diagnostic apparatus 10 and other devices in accordance with these various protocols. For this connection, electrical connection via an electronic network or the like can be applied. The network refers to a general information communication network using telecommunications technology and includes not only a wireless/wired LAN hospital backbone local area network (LAN) and the Internet network, but also a telephone communication network, an optical fiber communication network, a cable communication network, a satellite communication network, and other networks.

The processing circuitry 18 is configured to controls the entire operation of the ultrasonic diagnostic apparatus 10.

Further, the processing circuitry includes a processor configured to execute, by reading out and executing the program stored in the memory 16, a procedure for providing an image that includes a plurality of functional index values of the heart chamber and allows the user to easily and intuitively grasp the state of the cardiac function state.

The ultrasonic probe 20 is detachably connected to the ultrasonic diagnostic apparatus 10 via a cable. The ultrasonic probe 20 may be wirelessly connected to the ultrasonic diagnostic apparatus 10.

A two-dimensional array probe in which a plurality of ultrasonic transducers are arranged in the scanning direction (azimus direction) and a plurality of elements are arranged in the lens direction (elevation direction) can be used as the ultrasonic probe 20. Specifically, a 1.5D array probe, a 1.75D array probe, a 2D array probe, or the like can be used.

The ultrasonic probe 20 may be configured such that volume data can be acquired. In this case, the object may be scanned in three dimensions by the ultrasonic probe 20 which is a two-dimensional array type. The object may be scanned two-dimensionally by the ultrasonic probe 20 which is a one-dimensional type in which a plurality of piezoelectric oscillators are arranged in a row, or the object may be scanned in three dimensions by rotating the one-dimensional type probe or by mechanically swinging the piezoelectric oscillators in the one-dimensional type ultrasonic probe.

When the ultrasonic probe 20 can acquire volume data, the user can select between a two-dimensional display mode (2D mode) and a four-dimensional display mode (4D mode). The 2D mode is a mode in which any one of a plurality of two-dimensional ultrasonic images is displayed as a real-time moving image or a still image. The 4D mode is a mode for displaying a three-dimensional ultrasonic image acquired in real time as a moving image.

The input circuit 21 is realized by general input devices such as a trackball, a switch, a button, a mouse, a keyboard, a touch pad that performs an input operation by touching an operation surface, a contactless input circuit using an optical sensor, a voice input circuit, and the like. The input circuit 21 outputs an operation input signal corresponding to the operation of the user to the processing circuitry 18. The input circuit 21 may be configured as an operation panel. In this case, the operation panel functions as a touch command screen and may have a display, a touch input circuit provided in the vicinity of the display, and hard keys.

The display 22 is configured by a general display device such as a liquid crystal display or an OLED (Organic Light Emitting Diode) display, and displays information under the control of the processing circuitry 18. The ultrasonic diagnostic apparatus 10 may not include at least one of the input circuit 21 and the display 22.

when the ultrasonic diagnostic apparatus 10 is a stationary device and includes the input circuit 21 and the display 22, the input circuit 21 may function as a touch command screen. Further, when the ultrasonic diagnostic apparatus 10 is a tablet type or smartphone type ultrasonic diagnostic apparatus 10, the input circuit 21 and the display 22 may be integrated to form a touch panel.

Further, the ultrasonic diagnostic apparatus 10 may be connected to the medical image processing apparatus 30 and the image server 40 via the network N so as to be able to transmit to and receive data from each other.

Figure 2:
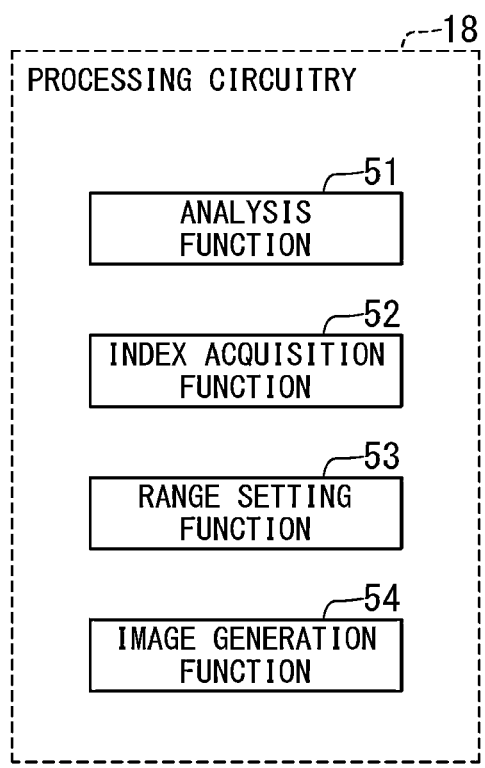
FIG. 2 is a block diagram showing an example of a function realized by a processor of processing circuitry.

FIG. 2 is a block diagram showing an example of a function realized by a processor of the processing circuitry 18. As shown in FIG. 2, the processor of processing circuitry 18 realizes the analysis function 51, the index acquisition function 52, the range setting function 53, and the image generation function 54. Each of these functions 51-54 is stored in memory 16 in the form of a program.

The analysis function 51 analyzes continuous multiple frame images of the heart of the object (hereinafter referred to as a cardiac moving image) to calculate function index values intrinsic to each heart chamber for two or more heart chambers including the left ventricle.

As the cardiac moving image, an image generated by the ultrasonic diagnostic apparatus 10 based on the data generated by the B mode processing circuit 12 or the Doppler processing circuit 13 may be used in real time or in a post process.

Further, the cardiac moving image may be generated by imaging an object with another modality such as an X-ray CT (Computed Tomography) apparatus or an MRI (Magnet Resonance Imaging) apparatus (not shown). The cardiac moving image generated by another modality may be obtained directly from the other modality via the network N or indirectly via the image server 40.

The function index value may be obtained by an information processing device such as a workstation or the medical image processing apparatus 30, or another ultrasonic diagnostic apparatus, or another modality by analyzing the cardiac moving image. In this case, the ultrasonic diagnostic apparatus 10 may not include the analysis function 51.

When the ultrasonic diagnostic apparatus 10 includes an analysis function 51, the analysis function 51 firstly acquires a 2D moving image or a 3D moving image including a heart chamber over at least one cardiac cycle of an object by, e.g., its own device. Subsequently, the analysis function 51 extracts a plurality of regions of interest in the heart chambers including the left ventricle in at least one or more initial phase of the cardiac moving image. Then, the analysis function 51 identifies the position in one cardiac cycle for each of the extracted region of interest of the heart chambers, and obtains the global cardiac function index from the position of the region of interest heart chambers in a predetermined cardiac time phase.

The 2D or 3D speckle-tracking echocardiography (STE) method is suitable as the position identification method. Global cardiac function indexes preferably include EF (Ejection Fraction in the left ventricle and Emptying Fraction in the left atrium), which is the rate of change in the lumen volume within the cardiac cycle, and global longitudinal strain (GLS), which is myocardial strain information. When using a 3D moving image, it is also possible to define a global area change ratio (GAC) with respect to the boundary surface of the intima or the middle layer.

The index acquisition function 52 is controlled by the image generation function 54, and acquires the function index value of each heart chamber included in the cardiac moving image. In the following description, an example will be shown in which the index acquisition function 52 acquires the function index value of each heart chamber for at least two heart chambers including the left ventricle depicted in the cardiac moving image.

The range setting function 53 sets predetermined normal range and abnormal range for the function index value. The normal range and the abnormal range of the function index value may be stored in the memory 16 in advance, or may be given by the user via the input circuit 21.

The image generation function 54 generates an image by superimposing a range suggestion image on a multidimensional coordinate space. In the two-dimensional coordinate space, the image generation function 54 allocates the function index value of each heart chamber to each display dimension corresponding to each heart chamber. In the range suggestion image, the image generation function 54 colors the range suggestion image according to the normal range and abnormal range predetermined for the functional index value of the predetermined heart chamber among the heart chambers. For example, the image generation function 54 firstly allocates the function index value of each heart chamber to the corresponding each display dimension to set the two-dimensional coordinate space in which the function index value of the left ventricle is defined as an output coordinate.

Then, the image generation function 54 generates the image in which the range suggestion image is superimposed on the two-dimensional coordinate space and displays the image on the display 22, where the range suggestion image is color-converted image that is colored in association with the normal and abnormal ranges that are predetermined with respect to the function index value of the left ventricle.

Each function 52-54 of the processing circuitry 18 may be provided in the medical image processing apparatus 30.

Further, the medical image processing apparatus 30 may include the analysis function 51. When the medical image processing apparatus 30 includes the analysis function 51, the medical image processing apparatus 30 acquires a cardiac moving image of an object from the ultrasonic diagnostic apparatus 10, the image server 40, or another modality via the network N, and obtains a function evaluation value. The medical image processing apparatus 30 generates an image in which the range suggestion image is superimposed on the two-dimensional coordinate space, and displays the image on an image display device such as the display 22 or a display of the medical image processing apparatus 30.

(Example of List Image of Character Strings)

An image including the function index values of a plurality of heart chambers generated by the conventional technique will be described.

Figure 3:
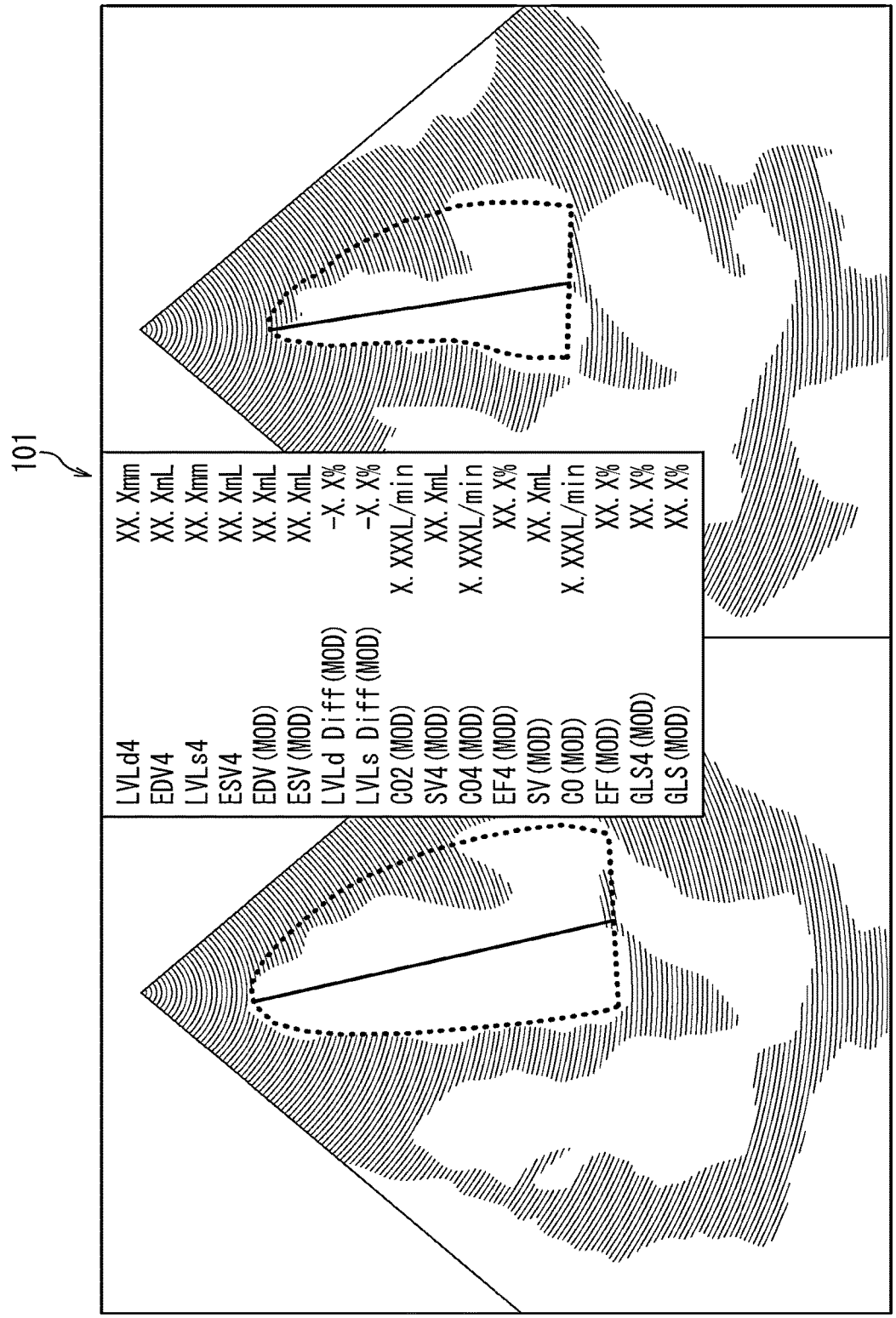
FIG. 3 is an explanatory diagram showing an example of a list image showing a plurality of function index values intrinsic to the left ventricle.

FIG. 3 is an explanatory diagram showing an example of a list image 101 showing a plurality of function index values intrinsic to the left ventricle.

As described above, in echocardiography using the ultrasonic diagnostic apparatus, cardiac function evaluation is performed using the function index value obtained by analyzing cardiac moving images of 2D moving image or 3D moving image. The function index value includes the volume information (End Diastolic Volume: EDV, End Systolic Volume: ESV, Ejection Fraction: EF) of the left ventricular (LV) by the modified-Simpson method, and the global longitudinal strain (GLS) information obtained by the speckle-tracking echocardiography (STE) method. It is known that EF and GLS information can be acquired by, for example, a fully automated Auto-EF application (see FIG. 3).

In addition to the left ventricle, for example, volume change rate (Emptying Fraction: EF) information and GLS information of the left atrium (LA) can be acquired and analyzed by the 2D-STE method using a 2D moving image. For the left ventricle, it is known that a three-dimensional EF using a 3D moving image, and strain information such as GLS and global area change ratio (GAC), can be obtained by the 3D-STE method.

In recent years, a cardiac function analysis function using a three-dimensional EF of the right ventricular (RV) and right atrium (RA) has also been provided. Further, acquisition of GLS by the 2D-STE method is possible in four cavities of LV, LA, RV and RA by using an A4C image. Still further, simultaneous analysis of multiple heart chambers using EF is also being provided recently.

However, when the function index values of multiple heart chambers are displayed on the screen at the same time, the displayed image becomes complicated and it becomes difficult for the user to grasp the desired function index value and the state of the cardiac function. For example, consider the case where the EF and GLS information and the cavity size information are displayed simultaneously for both the left ventricle and the left atrium. In this case, the list image of the left atrium, that is similar to the list image 101 consisting of only the function index values of the left ventricle shown in FIG. 3, is also displayed side by side on the screen at the same time as the list image 101. In this case, the user has to check a large number of character strings, and it is difficult for the user to grasp the cardiac function state of the object.

Additionally, since there are multiple definitions of EF and GLS in the atrium depending on the cardiac time phase, the output information is larger than that of the EF and GLS in the ventricle. For example, there are three types of EF (volume change rate) for the left atrium, i.e., total EF, active EF, and passive EF. Therefore, when displaying a plurality of types of EFs and GLSs of the atrium, the display becomes more complicated and it becomes difficult to evaluate and understand the cardiac function based on the function index value.

As a method of avoiding this kind of complexity when displaying the function index values of multiple heart chambers on the screen at the same time, a method of limiting the display items and displaying them at the same time can be adopted.

Figure 4:
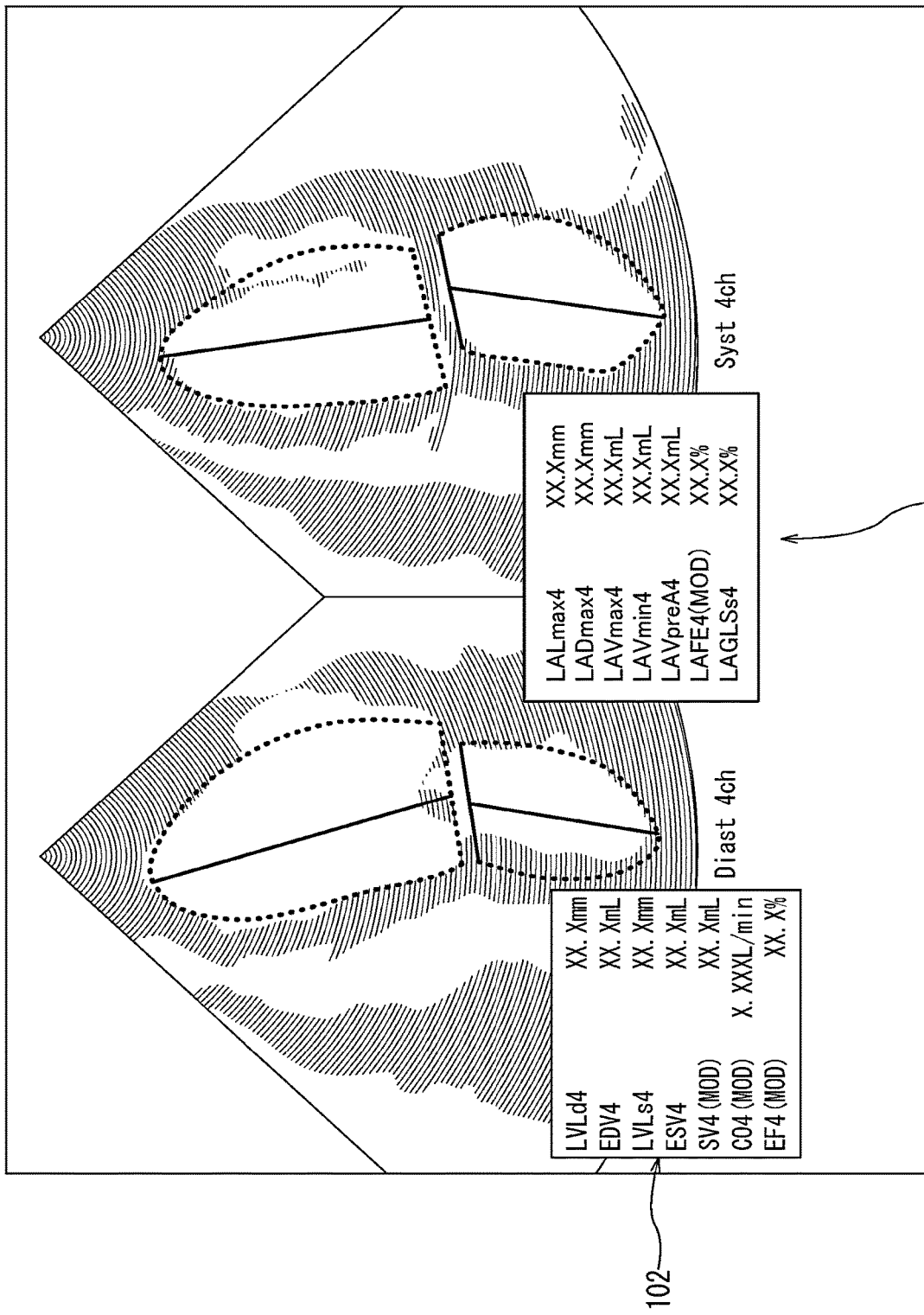
FIG. 4 is an explanatory diagram showing an example of list images, which are images including function index values of a plurality of heart chambers generated in the conventional technique, and in which listed items are limited.

FIG. 4 is an explanatory diagram showing an example of list images 102 and 103, which are images including function index values of a plurality of heart chambers generated in the conventional technique, and in which listed items are limited. In the example shown in FIG. 4, the list image 102 is an image showing a list of some items of the function index values of the left ventricle and the list image 103 is an image showing a list of some items of the function index values of the left atrium.

As shown in FIG. 4, by limiting the listed items to be displayed in the list images 102 and 103, the number of character strings can be reduced as compared with the case where two list images each corresponding to the list image 101 shown in FIG. 3 are displayed in parallel, and thus, the visibility of the user is improved. However, as is clear from FIG. 4, even if the listed items are limited, a large number of character strings are still listed on the screen, and it is still difficult for the user to grasp the cardiac function state of the object. Further, since the items shown in the list are limited, the available information is reduced and the diagnostic accuracy is deteriorated. Even when limiting the listed items, it is extremely difficult to intuitively understand the relationship between information of different heart chambers by comparing the list image 102 and the list image 103 in which only numerical values are simply listed.

Accordingly, the processing circuitry 18 of the ultrasonic diagnostic apparatus 10 according to the present embodiment generates an image including the function index values of a plurality of heart chambers such that the user can easily and intuitively grasp the cardiac function state and displays the image on the display 22.

(2D Plot)

Figure 5:
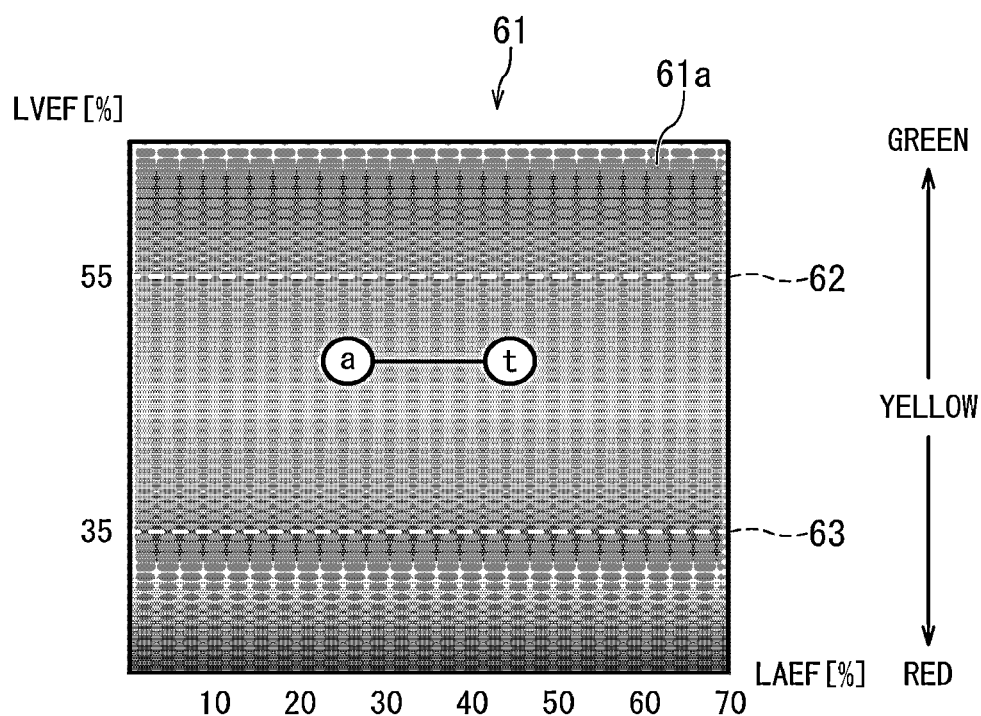
FIG. 5 is an explanatory diagram showing an example of a 2D cardiac function image according to the present embodiment.

FIG. 5 is an explanatory diagram showing an example of a 2D cardiac function image 61 according to the present embodiment. As shown in FIG. 5, the image generation function 54 may generate the 2D cardiac function image 61 in which the same global function index of multiple heart chambers is assigned to the corresponding display dimensions for corresponding heart chambers and are plotted in the two-dimensional coordinate space.

The 2D cardiac function image 61 shown in FIG. 5 uses the volume change rate (EF) as the same global cardiac function index, and the volume change rate of the left ventricle (left ventricular ejection fraction, LVEF) which is often considered important in the cardiac function evaluation is defined as the output dimension, and the volume change rate of the left atrium (LAEF) is plotted in the two-dimensional coordinate space defined as the input dimension. The volume change rate of the right ventricle (RVEF) may be used as the input dimension.

Further, the image generation function 54 superimposes the range suggestion image 61a, which is a color 2D mapping image color-converted according to the normal and abnormal range which are predetermined regarding the function index value assigned to the output dimension, on the two-dimensional coordinate space, and plots the function index on the range suggestion image 61a. In this case, the input dimension preferably has the range of values that the function index of the corresponding heart chamber can take. Note that, in FIG. 5, based on the guideline value of LVEF, an example is shown in which the normal range is 55% or more as the healthy value, while the abnormal range is 35% or less, which is the target value in cardiac resynchronization therapy, and the range suggestion image 61a using green, yellow, and red like a traffic signal is superimposed.

The image generation function 54 may superimpose an image showing predetermined ranges of normal and abnormal for each function index value on the 2D cardiac function image 61. FIG. 5 shows an example in which the normal threshold line 62 showing 55%, which is the threshold value of the normal range of the LVEF, and the abnormal threshold line 63 showing 35%, which is the threshold value of the abnormal range of the LVEF, are superimposed on the 2D cardiac function image 61.

Further, the image generation function 54 may label the type of volume change rates related to the atrial in the 2D cardiac function image 61 and plot volume change rates on the two-dimensional coordinate space at the same time. FIG.

5 shows an example in which the total-EF and active-EF of the left atrium are plotted by labeling the types of EF as "t" for total-EF and "a" for active-EF.

In this case, as shown in FIG. 5, the image generation function 54 may generate the selection acceptance image 64 for accepting the user's selection as to whether to plot multiple types of volume change rates at the same time or plot only one volume change rate and include selection acceptance image 64 in the 2D cardiac function image 61.

Here, the total-EF (Emptying Fraction) (EFt) of the left atrium is given by EFt=100*(Vmax−Vmin)/Vmax [%] (where V represents the volume of the left atrium). The active-EF (EFa) of the left atrium is given by EFa=100*(VpreA−Vmin)/VpreA [%]. Vmax (maximum volume), Vmin (minimum volume), and VpreA (volume before atrial systole) are determined from the time-varying curve of the volume of the left atrium in the cardiac cycle.

The atrial volume for the single A4C image and the single A2C image is plotted with the value of one cross section of the left ventricular LV and the left atrium LA. When synthesizing the results of the A4C image and the A2C image, both the left ventricular LV and the left atrium LA are plotted with the synthesized values by the modified Simpson method.

The time phase corresponding to VpreA is obtained by the method, in which the time-varying curve of volume is time-differentiated to obtain the zero-cross time phase in the late expansion period, disclosed by Zareian et al. (Journal of Cardiovascular Magnetic Resonance (2015) 17:52). When synthesizing the results of the A4C image and the A2C image, the VpreA time phase may be determined for each cross section and the synthesized VpreA value may be obtained by the modified Simpson method.

Further, the 2D cardiac function image 61 is preferably to be displayed at the same time as the ultrasonic image of the heart as shown in FIGS. 3 and 4. In this case, information indicating the position of the region of interest used for obtaining the function index may be displayed at the same time.

According to the 2D cardiac function image 61, the user can grasp the function index value extremely easily and intuitively without being bothered by the enumeration of numbers, as compared with the case where the numerical values of the function index values are enumerated. Further, since the range suggestion image 61a, which is a color 2D mapping image that has been color-converted for the normal and abnormal ranges, is superimposed on the 2D cardiac function image 61, the user can immediately grasp the cardiac function state of the object simply by visually recognizing the color of the range suggestion image 61a corresponding to the position of the plot.

Further, according to the 2D cardiac function image 61, the user can select whether to display the function index values of a plurality of types of the same heart chamber at the same time or to display only a single type via the selection acceptance image 64. Further, even when displaying a plurality of types of function index values of the same heart chamber at the same time, according to the 2D cardiac function image 61, the user can easily and intuitively grasp the relationship between the function index values of each type, and immediately grasp the cardiac function state of the object simply by visually recognizing the color of the range suggestion image 61a corresponding to the position of each plot.

Figure 6:
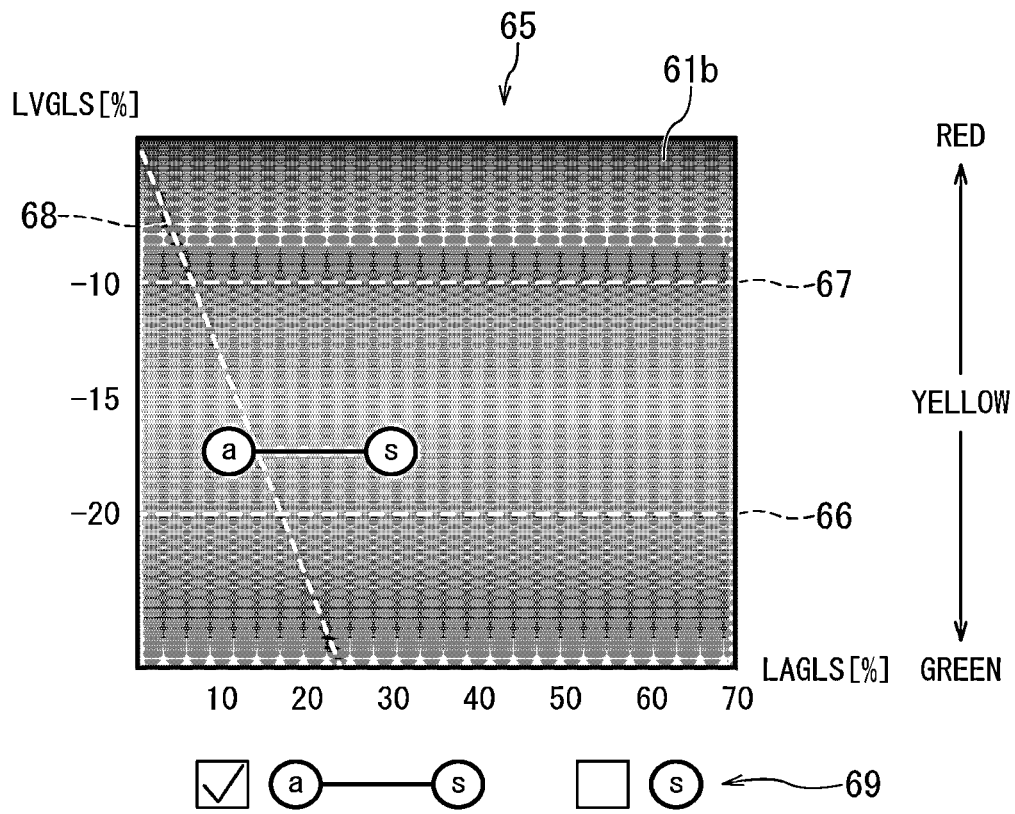
FIG. 6 is an explanatory diagram showing an example of a variation of the 2D cardiac function image.

FIG. 6 is an explanatory diagram showing an example of the variation image 65 of the 2D cardiac function image 61.

The variation image 65 of the 2D cardiac function image 61 is an example of an image when GLS, which is one of the strain indexes, is plotted as the same global cardiac function index in the two-dimensional coordinate space in which the GLS of the left ventricle is defined as the output dimension and the GLS of the left atrium is defined as the input dimension.

Further, in the same manner as the 2D cardiac function image 61, the range suggestion image 61b is preferable to be superimposed on the variation image 65, where the range suggestion image 61b is colored green, yellow, and red like a traffic signal to show that the normal range is −20% or less, which is the healthy value based on the guideline value of LVGLS, and the abnormal range is −15% (or −10%) or more, which is regarded abnormal for various index types. Further, the image generation function 54 may superimpose the normal threshold line 66 and the abnormal threshold line 67 of the LVGLS on the variation image 65 in the same manner as the 2D cardiac function image 61 (see FIG. 6).

As shown in FIG. 6, the image generation function 54 may further superimpose the straight line 68 of LVGLS=−LAGLS on the variation image 65. In this case, the user can more easily grasp the relationship between both plot positions.

Further, in the variation image 65 of the 2D cardiac function image 61, the image generation function 54 may plot the strain index of each time phase of the ventricular systole (s-phase) and the atrial systole (a-phase) related to the atrium on the two-dimensional coordinate space at the same time by labeling the time phase type. FIG. 6 shows an example in which the time phase types of LAGLS are labeled and plotted as "s" for LAGLSs and "a" for LAGLSa.

Similar to the 2D cardiac function image 61, in the variation image 65, selection acceptance image 69 for accepting the user's selection as to whether to plot a plurality of types of LAGLS at the same time or plot only one of them as shown in FIG. 6 can be included.

Here, LAGLSs is a peak value (maximum value) of systole. LAGLSa is given by LAGLSa=LAGLSs−Sa' where the value of the a' time phase (VpreA phase) is Sa'.

The atrial volume for the single A4C image and the single A2C image is plotted with the value of one cross section of the left ventricular LV and the left atrium LA. When synthesizing the results of the A4C image and the A2C image, it is preferable to plot with the average GLS value of both the left ventricular LV and the left atrium LA.

Further, the image generation function 54 may generate a plurality of two-dimensional coordinate spaces in which at least one of the function index values assigned to the display dimensions is different from each other and display the two-dimensional coordinate spaces in parallel on the display 22.

Specifically, the image generation function 54 may generate both the 2D cardiac function image 61 and the variation image 65 and display them in parallel on the display 22.

Although the variation image 65 shows an example in which GLS is used as the same global strain index, another function index value such as GAC may be used as the same global strain index.

The variation image 65 shown in FIG. 6 can also obtain the same effect as the 2D cardiac function image 61.

(3D Plot)

Figure 7:
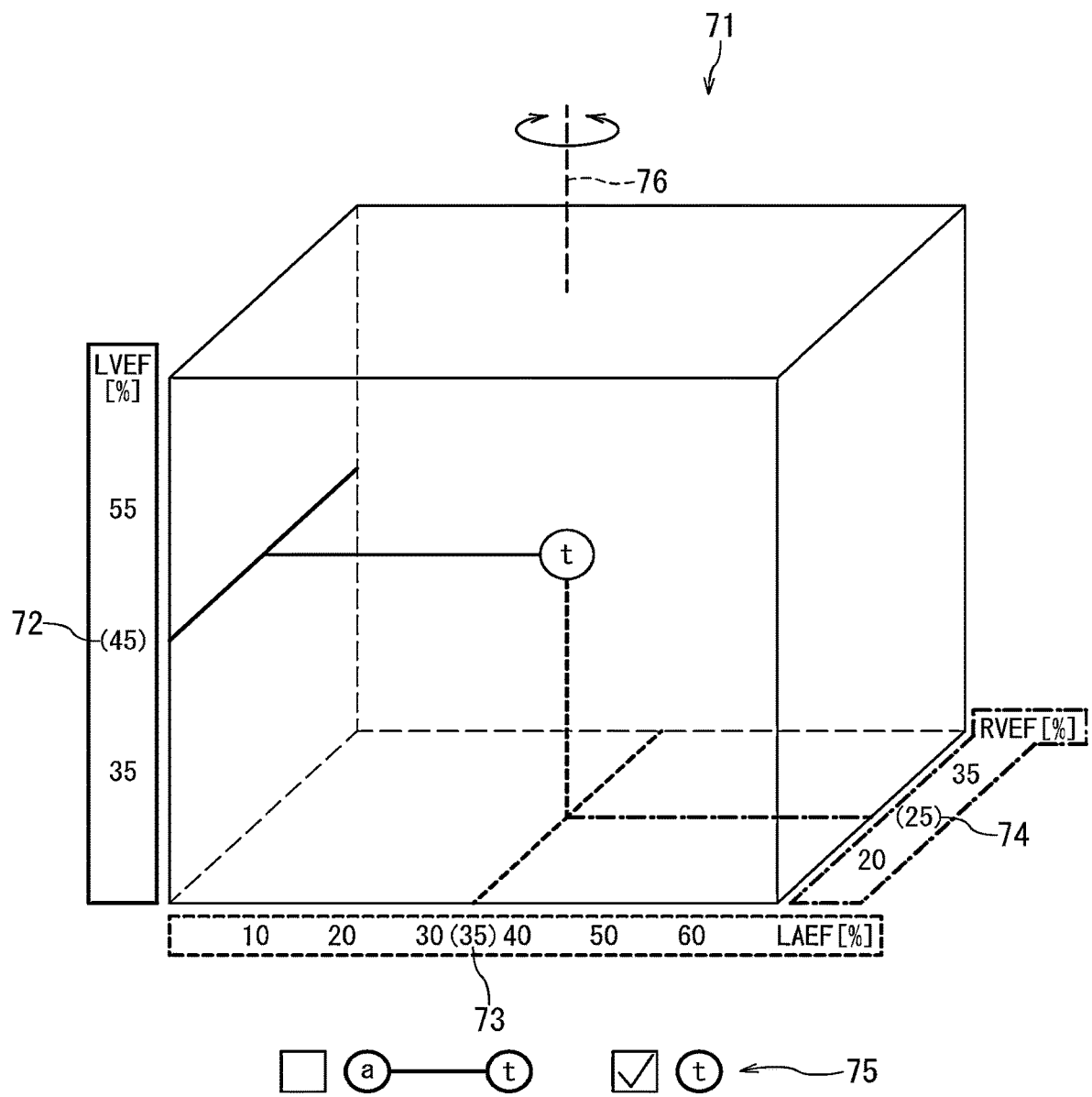
FIG. 7 is an explanatory diagram showing an example of a 3D cardiac function image according to the present embodiment.

FIG. 7 is an explanatory diagram showing an example of the 3D cardiac function image 71 according to the present embodiment.

As shown in FIG. 7, the image generation function 54 may generate the 3D cardiac function image 71 in which the same global heart function index is assigned to the display dimension for each heart chamber and plotted in the three-dimensional coordinate space. In this case, the image generation function 54 assigns the function index value of the left ventricle to ordinate (for example, z-axis) and the function index values of the other two heart chambers to two axes (for example, x-axis and y-axis) orthogonal to ordinate to set a three-dimensional coordinate space.

The 3D cardiac function image 71 shown in FIG. 7 is an example of an image when the volume change rate (EF) is plotted as the same global cardiac function index in the three-dimensional coordinate space in which the EF of the left ventricle is assigned to ordinate as the output dimension and fixed, and the EF of the left atrium and the EF of the right ventricle are assigned as input dimensions.

The 3D cardiac function image 71 includes images 72, 73, 74 for emphasizing the values on each axis in order to make it easier to grasp the function index value corresponding to the plot position. FIG. 7 shows an example when the image for emphasizing is "( )" (see "(45)" of LVEF in FIG. 7, "(35)" of LAEFt, and "(25)" of RVEF). The image for emphasizing may be a figure surrounding the value corresponding to the plot position. As a method of emphasizing the value corresponding to the plot position, the display mode (size, font, thickness, brightness, and the like) of the value corresponding to the plot position may be different from other values, instead of the images 72, 73, 74.

Perpendicular lines colored in different colors may be added from the plot to each axis. In FIG. 7, the line types are different, such as straight lines, dashed lines, and alternate long and short dash lines to show that each perpendicular line has a different color. Further, by setting the color of the character string of the value of each axis and the character string of the label of each axis to the same color as the color of the perpendicular line, the user can easily grasp the function index value corresponding to the plot position. In FIG. 7, the solid line surrounding the area including "LVEF" is a line illustrated for convenience of explaining that the character strings in the area within the solid line are colored in the same color, and this surrounding solid line is not actually displayed on the display 22. The same applies to the broken line surrounding the region containing "LAEF" and the alternate long and short dash line surrounding the region containing "RVEF".

One axis of the 3D cardiac function image 71 shown in FIG. 7 is the volume change rate (LAEF) of the left atrium, which is the function index value in which a plurality of types are defined. Therefore, as in FIGS. 5 and 6, the image generation function 54 may plotted the value by labeling the types of LAEFt and LAEFa in the 3D cardiac function image 71. Further, the selection acceptance image 75 for accepting the user's selection as to whether to plot both types at the same time or plot only one type may be generated and included in the 3D cardiac function image 71.

The 3D cardiac function image 71 shown in FIG. 7 can also obtain the same effect as the 2D cardiac function image 61. Further, according to the 3D cardiac function image 71, since the function index values of the three heart chambers can be confirmed at once, the cardiac function state of the object can be grasped more accurately than the 2D cardiac function image 61. Further, according to the 3D cardiac function image 71, although the function index values of the three heart chambers are displayed at the same time, the user is not bothered by the enumeration of numbers as in the conventional image.

Figure 8:
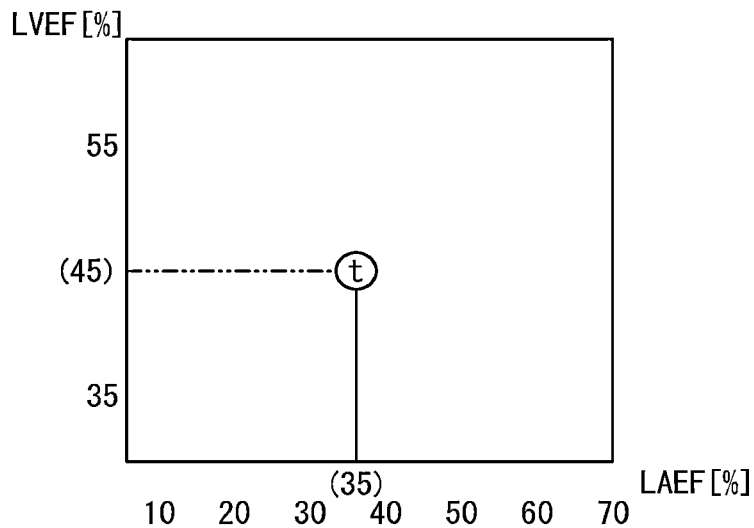
FIG. 8 is an explanatory diagram showing an example of a 2D cardiac function image displayed as a transition image when the 3D cardiac function image is rotated around an axis parallel to the ordinate.
Figure 8:
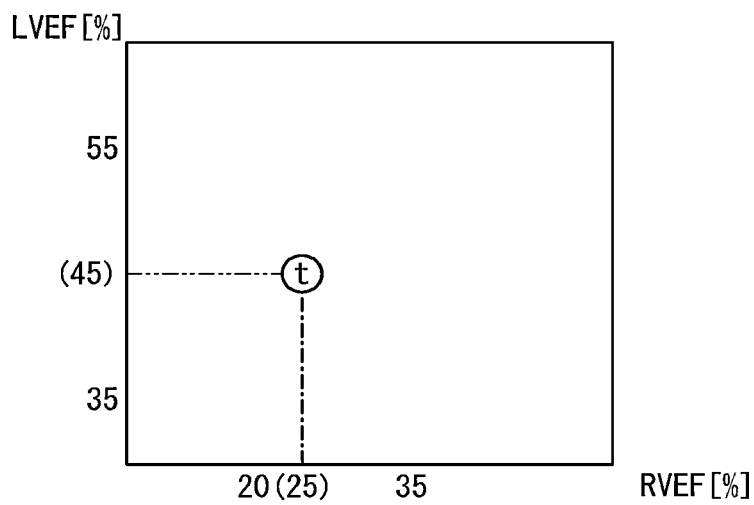

FIG. 8 is an explanatory diagram showing an example of a 2D cardiac function image displayed as a transition image when the 3D cardiac function image 71 is rotated about the axis 76 as a central axis.

The image generation function 54 may generate an image such that the 3D cardiac function image 71 is rotated at an angle according to a user instruction, with the axis 76 parallel to the ordinate of the 3D cardiac function image 71 as the central axis.

Further, the image generation function 54 may be able to change the viewpoint of the 3D cardiac function image 71 in response to a user instruction via the input circuit.

Consider a case where the viewpoint of the 3D cardiac function image 71 is set from the front side instead of the oblique viewpoint of the cube (see FIG. 7). When the 3D cardiac function image 71 is rotated about the axis 76 parallel to the ordinate as the central axis, the 2D cardiac function image with only LAEF as the horizontal axis appears when the RVEF is parallel to the depth direction. Similarly, when LAEF is parallel to the depth direction, the 2D cardiac function image whose horizontal axis shows only RVEF appears. (See FIG. 8).

It can be said that these 2D cardiac function image corresponds to the 2D cardiac function image 61 shown in FIG. 5. Therefore, the image generation function 54 may superimpose the range suggestion image 61a (see FIG. 5), which is a color 2D mapping image, on the 2D cardiac function image that appears by rotating the 3D cardiac function image 71 around the axis 76.

By making the 3D cardiac function image 71 rotatable around the axis 76, the user can display the function evaluation values of the three heart chambers at the same time (see FIG. 7), and the function evaluation values of the two desired heart chambers can be also displayed on the 2D cardiac function image (see FIG. 8). When the range suggestion image 61a is superimposed on the 2D cardiac function image that appears by rotating the 3D cardiac function image, the user can display the function evaluation values of the three heart chambers at the same time to grasp the whole, or display the 2D cardiac function image to confirm the positional relationship between the range suggestion image 61a and the plot, thereby easily grasping the cardiac function state of an object.

Figure 9:
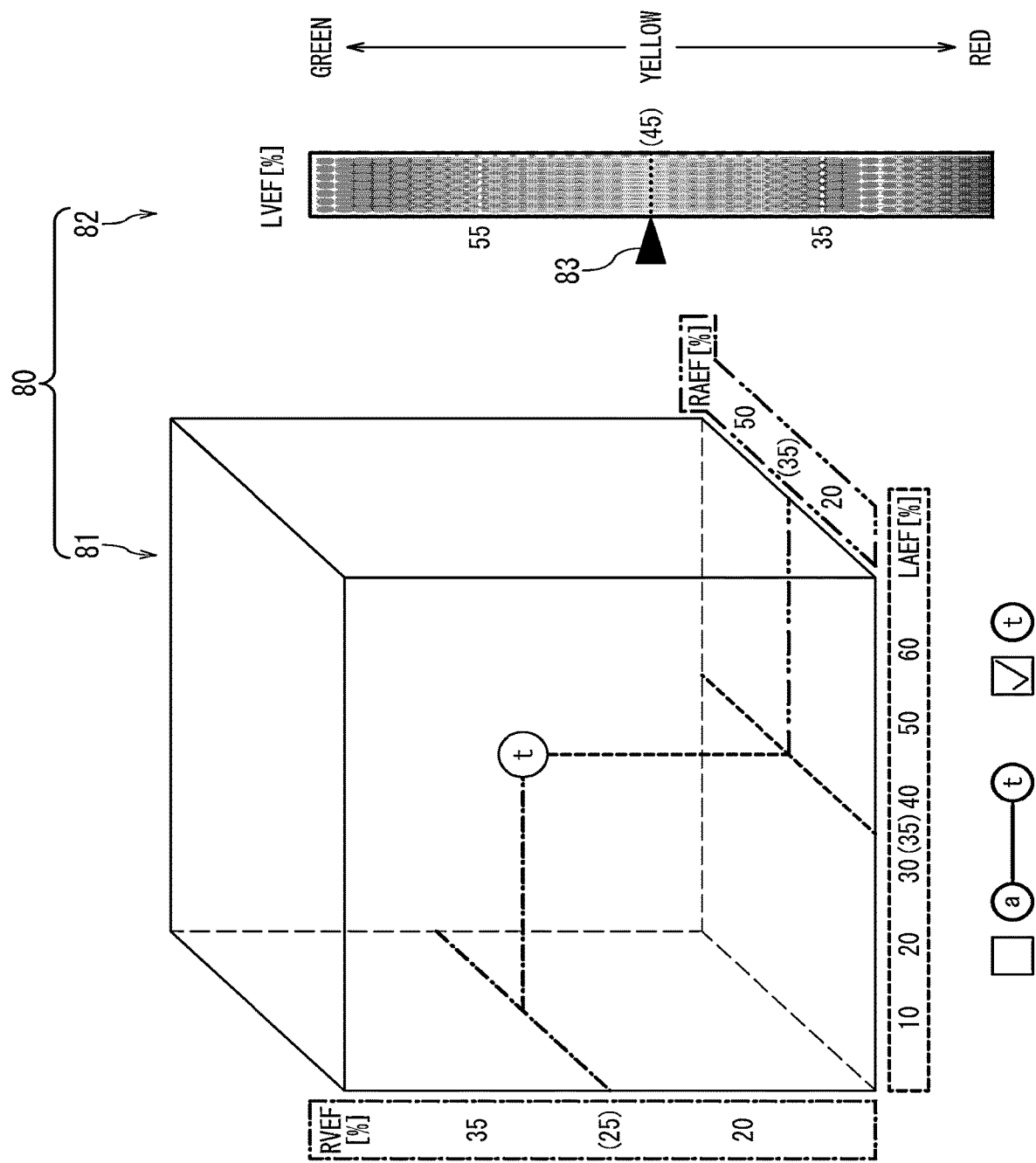
FIG. 9 an explanatory diagram showing an example of a variation of the 3D cardiac function image.

FIG. 9 is an explanatory diagram showing an example of the variation image 80 of the 3D cardiac function image 71.

The variation image 80 of the 3D cardiac function image 71 includes the 3D cardiac function image 81 and the LVEF value image 82 showing the EF of the left ventricle. In the 3D cardiac function image 81, the EF of the left atrium is used instead of the EF of the left ventricle assigned to the ordinate of the 3D cardiac function image 71, and the EFs of the right atrium, the right ventricle, and the left atrium are assigned to each axis. The EF assigned to the ordinate is preferably the EF of the left atrium or the right ventricle. The two-dot chain line in the 3D cardiac function image 81 of the variation image 80 indicates that the line corresponds to a color different from the straight line and the broken line. In this case, the 3D cardiac function image 81, that indicates the EF of the right atrium, the right ventricle, and the left atrium, and the LVEF value image 82 are simultaneously displayed, for example, in parallel in the variation image 80 (see FIG. 9).

The image generation function 54 generates at least one of a character string showing the EF of the left ventricle, an image having brightness corresponding to the EF of the left ventricle, and an image having a color corresponding to the EF of the left ventricle, as the LVEF value image 82 showing the EF of the left ventricle. FIG. 9 shows an example in which the LVEF value image 82 is a color bar corresponding to the EF of the left ventricle and is colored in the same manner as the range suggestion image 61a.

On the LVEF value image 82, the image generation function 54 may superimpose a normal threshold line and an abnormal threshold line, or an image for emphasizing the LVEF value corresponding to the plot on the 3D cardiac function image 81 (see "(45)" of LVEF value image 82 in FIG. 9). Further, the image generation function 54 may superimpose on the LVEF value image 82 an image 83 (see the arrow in FIG. 9) showing the position of the LVEF value on the LVEF value image 82 corresponding to the plot of the 3D cardiac function image 81.

The variation image 80 of the 3D cardiac function image 71 shown in FIG. 9 can also obtain the same effect as the 3D cardiac function image 71. Further, according to the variation image 80, since the function index values of the four heart chambers can be confirmed at once, the user can grasp the cardiac function state of the object more accurately than the 3D cardiac function image 71. Further, according to the variation image 80, although the function index values of the four heart chambers are displayed at the same time, the user is not bothered by the enumeration of numbers as in the conventional image.

(Time Series Display)

Figure 10:
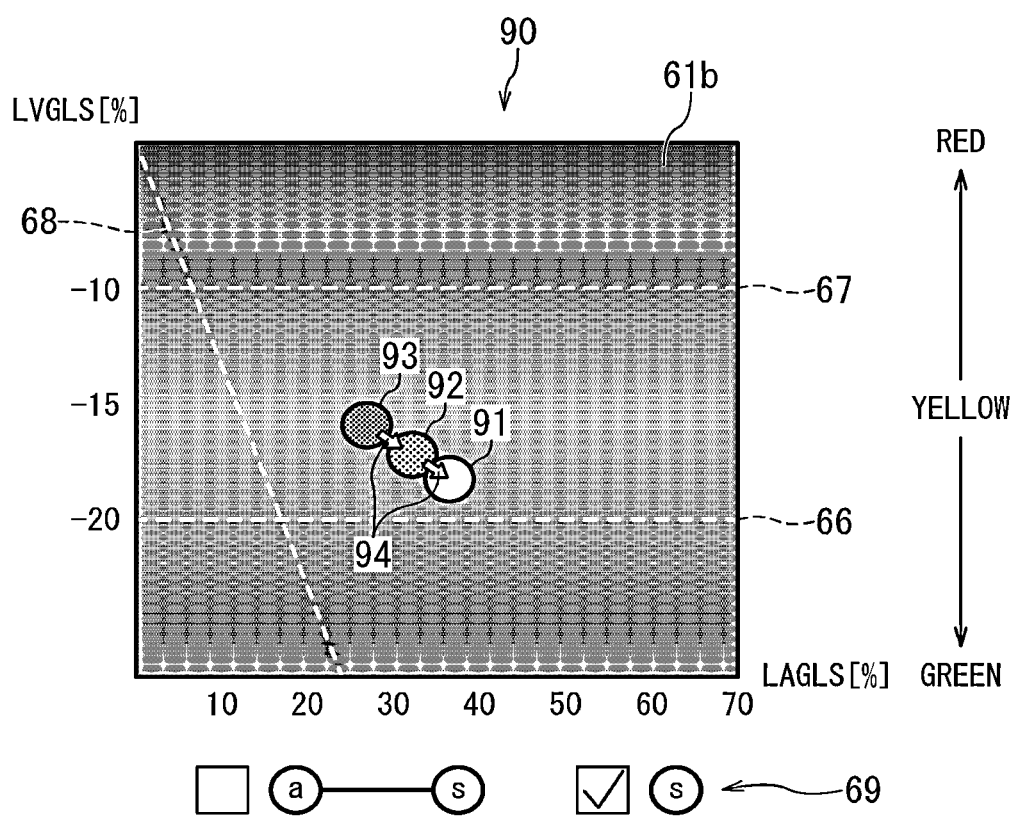
FIG. 10 is an explanatory diagram showing an example of a time series image according to the present embodiment.

FIG. 10 is an explanatory diagram showing an example of the time series image 90 according to the present embodiment.

The image generation function 54 can simultaneously plot a plurality of function index values having different time series from each other, which are obtained based on moving images of the heart taken in different time series such as before and after treatment or before and after applying loads of stress echo for the same object. FIG. 10 shows an example in which three plots 91, 92 and 93 are simultaneously displayed on the variation image 65 of the 2D cardiac function image 61 shown in FIG. 6 in the order of corresponding time series.

The plurality of plots 91, 92, and 93 having different time series from each other may be labeled based on such differences in time series. FIG. 10 shows an example in which each plot is hatched thinner as the corresponding time series is closer to the present time, whereby the newer the corresponding time series, the brighter the user visually recognizes the plot. Further, the image generation function 54 may further superimpose an image showing the time lapse direction between the plurality of plots 91, 92, 93 having different time series. FIG. 10 shows an example in which the arrow 94 is superimposed as an image showing the time passage direction.

According to the time series image 90, a plurality of function index values having different time series can be confirmed at the same time. Therefore, the user can easily and intuitively grasp the time change of the function index value of the object. Further, by confirming the color change of the range suggestion image 61b corresponding to each position of the plurality of plots having different time series from each other, the time change of the cardiac function state of the object can be immediately grasped. Therefore, according to the time series image 90, the user can easily and accurately diagnose the object, evaluate the past treatment plan, formulate the future treatment plan, and set the load in the stress echo.

Although FIG. 10 shows an example in which the display of a plurality of plots having different time series is applied to the 2D cardiac function image, the display of the plurality of plots having different time series may be applied to the 3D cardiac function image such as the 3D cardiac function image 71 and the variation image 80.

According to at least one embodiment described above, it is possible to provide an image that includes a plurality of functional index values of the cardiac cavity and allows the user to easily and intuitively grasp the state of the cardiac function.

The term "processor" used in the explanation in the above-described embodiments, for instance, refers to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing the corresponding program. When a plurality of processors are provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
processing circuitry configured to
acquire a first function index value related to a first heart chamber and a second function index value related to a second heart chamber, wherein at least one of the first and second heart chambers include a left ventricle, and are included in a moving image of a heart;
generate a two-dimensional cardiac function image in which the first and second function index values related to the first and second heart chambers are plotted at a coordinate position determined by the first and second function index values in a two-dimensional coordinate space defined by a first axis and a second axis orthogonal to the first axis; and
superimpose a range suggestion image, in which a normal range and an abnormal range with respect to one of the first and second indexes are indicated with different colors, on the two-dimensional cardiac function image,
wherein the processing circuitry is further configured to
acquire a third function index value related to a third heart chamber;
set a three-dimensional coordinate space in which the first, second, and third function index values are plotted at a particular coordinate position, the three-dimensional coordinate space being defined by the first and second axes, and a third axis orthogonal to both the first and second axes, wherein the first function index is related to the left ventricle, and the second and third function indices are related to two other heart chambers; and
generate a three-dimensional cardiac function image based on the set three-dimensional coordinate space.

2. The ultrasonic diagnostic apparatus according to claim 1, wherein the two other heart chambers are a right ventricle and a left atrium.

3. The ultrasonic diagnostic apparatus according to claim 1, wherein the processing circuitry is further configured to generate the two-dimensional cardiac function image by rotating the three-dimensional cardiac function image of the three-dimensional coordinate space at an angle according to a user instruction.

4. The ultrasonic diagnostic apparatus according to claim 1, wherein the processing circuitry is further configured to:
acquire a function index value of a remaining heart chamber of four heart chambers;
set a second three-dimensional coordinate space in which a right atrium, a right ventricle, and a left atrium are assigned to each display dimension;
generate a second three-dimensional cardiac function image based on the set second three-dimensional coordinate space, and
display both the three-dimensional cardiac function image and the second three-dimensional cardiac function image side by side on a display.

5. The ultrasonic diagnostic apparatus according to claim 1, wherein
one of the first and second function index values is a function index value of the left ventricle, and
the processing circuitry is further configured to generate the two-dimensional cardiac function image such that the function index value of the left ventricle is indicated by at least one of a character string, a brightness, and a color.

6. The ultrasonic diagnostic apparatus according to claim 1, wherein one of the function index values of the first and second heart chambers includes a left ventricular ejection fraction.

7. The ultrasonic diagnostic apparatus according to claim 1, wherein one of the function index values of the first and second heart chambers includes a global longitudinal strain.

8. The ultrasonic diagnostic apparatus according to claim 1, wherein one of the function index values of the first and second heart chambers includes a global area change ratio.

9. The ultrasonic diagnostic apparatus according to claim 1, wherein the processing circuitry is further configured to generate a plurality of coordinate spaces in which at least one of the function index values assigned to a display dimension is different from another of the function index values, and display the plurality of coordinate spaces side by side on a display.

10. The ultrasonic diagnostic apparatus according to claim 1, wherein the processing circuitry is further configured to:
acquire, as the first and second function index values, a plurality of function index values having different time series from each other, which are obtained based on moving images of the heart obtained by imaging a same object in the different time series; and
generate an image such that the plurality of function index values having different time series from each other are labeled for each time series and simultaneously shown in the two-dimensional coordinate space.

11. The ultrasonic diagnostic apparatus according to claim 10, wherein the processing circuitry is further configured to superimpose an image indicating a time lapse direction between the function index values on the image generated such that the function index values having different time series from each other are labeled for each time series and simultaneously shown in the two-dimensional coordinate space.

12. A medical image processing apparatus, comprising:
processing circuitry configured to
acquire a first function index value related to a first heart chamber and a second function index value related to a second heart chamber, wherein at least one of the first and second heart chambers include a left ventricle and are included in a moving image of a heart;
generate a two-dimensional cardiac function image in which the first and second function index values related to the first and second heart chambers are plotted at a coordinate position determined by the first and second function index values in a two-dimensional coordinate space defined by a first axis and a second axis orthogonal to the first axis; and
superimpose a range suggestion image, in which a normal range and an abnormal range with respect to one of the first and second indexes are indicated with different colors, on the two-dimensional cardiac function image,
wherein the processing circuitry is further configured to
acquire a third function index value related to a third heart chamber;
set a three-dimensional coordinate space in which the first, second, and third function index values are plotted at a particular coordinate position, the three-dimensional coordinate space being defined by the first and second axes, and a third axis orthogonal to both the first and second axes, wherein the first function index is related to the left ventricle, and the second and third function indices are related to two other heart chambers; and
generate a three-dimensional cardiac function image based on the set three-dimensional coordinate space.

13. A medical image processing method, comprising:
acquiring a first function index value related to a first heart chamber and a second function index value related to a second heart chamber, wherein at least one of the first and second heart chambers include a left ventricle and are included in a moving image of a heart;
generating a two-dimensional cardiac function image in which the first and second function index values related to the first and second heart chambers are plotted at a coordinate position determined by the first and second function index values in a two-dimensional coordinate space defined by a first axis and a second axis orthogonal to the first axis; and superimposing a range suggestion image, in which a normal range and an abnormal range with respect to one of the first and second indexes are indicated with different colors, on the two-dimensional cardiac function image, wherein the method further comprises
acquiring a third function index value related to a third heart chamber;
setting a three-dimensional coordinate space in which the first, second, and third function index values are plotted at a particular coordinate position, the three-dimensional coordinate space being defined by the first and second axes, and a third axis orthogonal to both the first and second axes, wherein the first function index is related to the left ventricle, and the second and third function indices are related to two other heart chambers; and
generating a three-dimensional cardiac function image based on the set three-dimensional coordinate space.

14. The medical image processing method of claim 13, wherein the first axis represents values of the first function index and the second axis represents values of the second function index.

\* \* \* \* \*